Oct. 4, 1955 W. L. SPANDIKOW, JR Plant Pat. 1,423
ROSE PLANT
Filed July 13, 1953
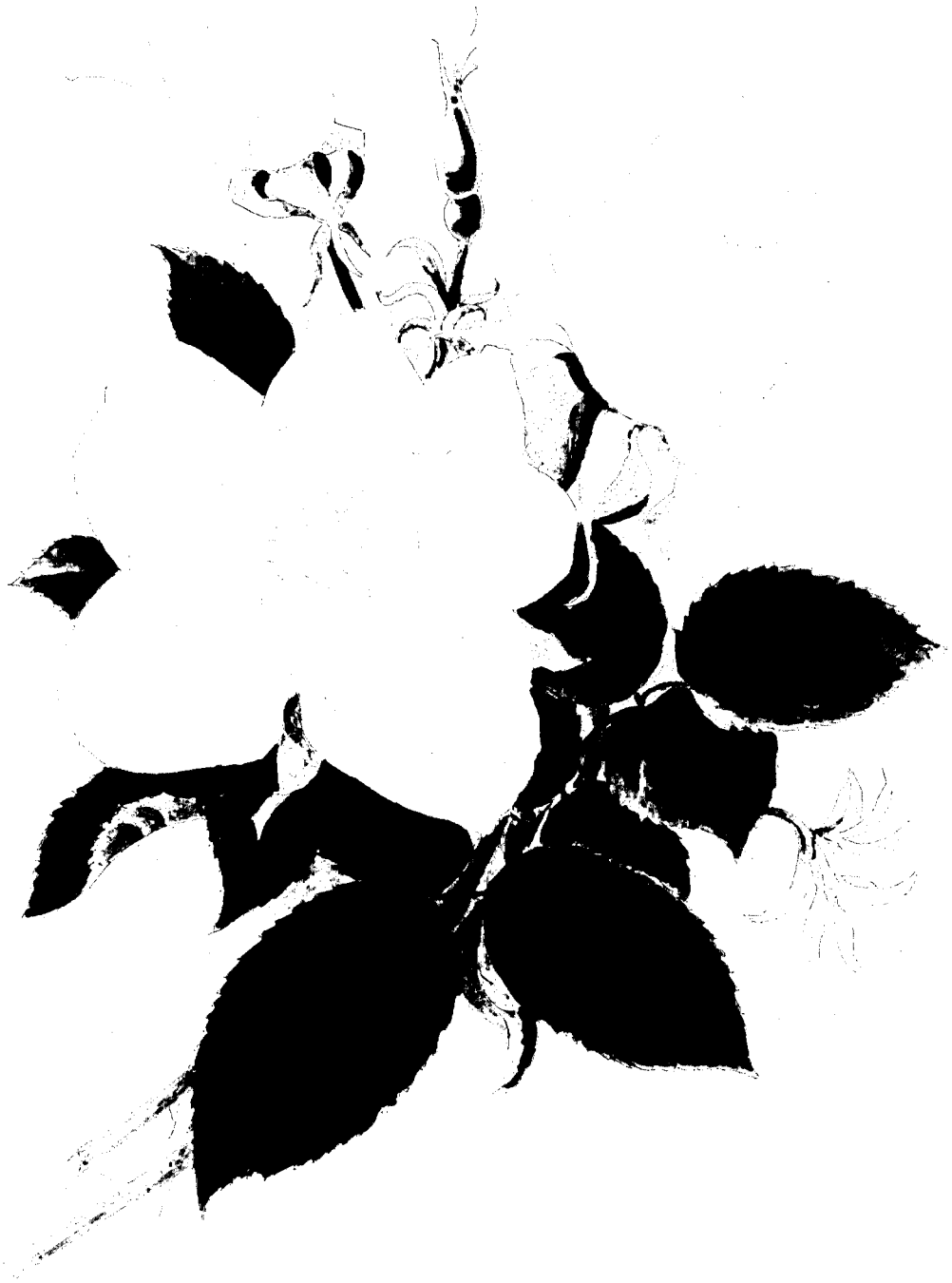
WITNESS
Addison E. Avery
INVENTOR
William L. Spandikow, Jr.
Rummler & Rummler & Snow,
ATTYS.

United States Patent Office

Plant Pat. 1,423
Patented Oct. 4, 1955

1,423

ROSE PLANT

William L. Spandikow, Jr., Batavia, Ill., assignor to William Spandikow Company, Chicago, Ill., a corporation of Illinois Application July 13, 1953, Serial No. 367,778

1 Claim. (Cl. 47—61)

The present invention relates to a new and distinct variety of rose plant of the hybrid tea class, which originated as a seedling resulting from cross pollinization of the well-known variety named "Madam Butterfly" (unpatented) with the variety named "Sally" (Plant Patent No. 187).

This new variety of hybrid tea rose plant is the result of breeding efforts carried on by me since 1951 in my greenhouses at Batavia, Kane County, Illinois, with a view to obtaining a superior variety having blooms of soft pink coloring and non-fading character.

Asexual reproduction of this new variety by budding at Batavia, Illinois, shows that the novel characteristics come true to form and are maintained through succeeding propagations.

This new variety of rose possesses characteristics differing from both parent plants, mainly in respect to size and color of its blooms and being more disease resistant. Its production of blooms per plant is about the same as "Madam Butterfly"; its buds are 100% larger; and its leaves are longer and more sharply pointed. Its blooms have a more intense pink color at the center than those of "Sally"; they have shorter, more slender and smoother stems; and the thorns are about the same in amount but are smaller than those of "Sally."

These characteristics, as well as other important ones, are set forth in the following detailed description:

Class: Hybrid tea.
Origin: Hybrid seedling.
*Seed parent.*—"Madam Butterfly" (unpatented).
*Pollen parent.*—"Sally" (Plant Patent #187).

Result of definite breeding efforts carried on by me and my associates at Batavia, Illinois, in 1951.

Plants have been reproduced asexually since 1951 mainly by budding, at Batavia, Illinois.

Plant:
*Form.*—Bush.
*Height.*—Depends on age; 1½ feet at 6 months. Abundant foliage.
*Growth.*—Vigorous and branching.
Flower:
*Blooming habit.*—Continuous and profuse all year round in greenhouse. 25 to 30 flowers per plant per year.
*Size.*—4 to 6 inches in diameter.
*Borne.*—Singly.
*Shape.*—High center when bud first opens, then urn-shape, then in mature bloom the petals spread showing depressed center of more intensely pink petaloids covering the genital organs.
*Petalage.*—49 to 52 including petaloids.
*Main petals.*—Ovate-shape.

*Color.*—Pink outer areas merging to yellow at base. No discoloration, paler pink when aging.
Texture of petals soft and silky.
Petals do not fall off but tend to hang on until dry.
Sides of petals curl outward to form pointed tips in fully opened flower. After blooms mature, petaloids spread and expose large group of pistils surrounded by many stamens. These are not shown in the drawings.

Blooms are disease resistant. This variety is fairly free from mildew but will get it under severe conditions. It is completely free from blackspot.
Fragrance, very slight.
*Buds.*—Shape, long and tapering. Large upon opening, urn-shaped when partly open. Color, predominately Opera Pink to Cherry Bloom, blending to yellow base.
*Sepals.*—Long and spear-shape with spatulate ends. Tenaciously hooding over the bud and then dropping straight down when bud starts to open. Do not fall off.
*Calyx.*—Small, funnel-shape. Aspect, smooth.
*Peduncle.*—Averages 4½ inches in length. Smooth.
*Foliage.*—Abundant. Flat green. Large leaves, 3 inches long by 1½ inches wide. Texture, leathery. Smooth on upper side and rough on under side. *Shape.*—Lanceolate with finely serrated edges. Petioles, short.
*Genital organs.* — Stamens, reddish-brown with Florida Gold anthers, about 175 in number. Pistils, red with white stigmas. Ovaries, weak, poor for reproduction.

The accompanying painting shows the general appearance of the blooms and foliage, including buds and mature flower.

Distinguishing identification of colors according to Maerz and Paul's Dictionary of Color, Edition of 1930, is as follows:

| Item | Plate | Letter | No. |
|---|---|---|---|
| Flower: | | | |
| Outer areas of petals, lightest shade | 1 | A | 1 |
| merging to | 1 | A | 8 |
| Center of opening bud | 1 | F | 7 |
| Center of open bloom | 1 | I | 8 |
| shading into | 1 | I | 9 |
| Darker shades in center of bloom | 4 | K | 9 |
| Yellow base, both outside and inside | 10 | K | 5 |
| shading into | 10 | K | 8 |
| Foliage, main leaf green | 24 | L | 9 |

The flowers are relatively long-lasting; their permanence on the plant is excellent, the petals do not fall off but dry up on the cut blooms. These characteristics, combined with the bushy, dense growth of the foliage, compactness of petals in the flower, slender but sturdy stems, superior keeping qualities, resistance to blackspot and weather enhance the value of this plant as a commercial product, and distinguish it from other known varieties.

I claim:

A new and distinct variety of rose plant of the hybrid tea class, substantially as herein shown and described, characterized as to novelty by its vigorous bushy habit of growth, sturdy stems, by its profuse flowering habit with large buds and flowers, by its distinctively pink shades blending into yellow coloring at the base of the petals, and by its superior keeping qualities.

No references cited.